United States Patent [19]

Chen et al.

[11] Patent Number: 5,916,812
[45] Date of Patent: *Jun. 29, 1999

[54] TEST SAMPLE CARD WITH POLYMETHYLPENTENE TAPE

[75] Inventors: Patrick K. Chen, Chesterfield, Mo.; Raymond E. O'Bear, Granite City, Ill.

[73] Assignee: bioMerieux, Inc., Hazelwood, Mo.

[ * ] Notice: This patent is subject to a terminal disclaimer.

[21] Appl. No.: 08/855,199

[22] Filed: May 13, 1997

Related U.S. Application Data

[63] Continuation-in-part of application No. 08/455,404, May 31, 1995, Pat. No. 5,800,778.

[51] Int. Cl.$^6$ .................................................. B65B 7/28
[52] U.S. Cl. ............................. 436/18; 156/69; 53/376.5; 422/102
[58] Field of Search ........................... 422/99, 102, 103; 156/69, 292, 252, 256; 53/452, 456, 376.5; 436/18

[56] References Cited

U.S. PATENT DOCUMENTS

| | | |
|---|---|---|
| 3,963,355 | 6/1976 | Aldridge, Jr. et al. . |
| 4,038,151 | 7/1977 | Fadler et al. . |
| 4,116,775 | 9/1978 | Charles et al. . |
| 4,118,280 | 10/1978 | Charles et al. . |
| 4,318,994 | 3/1982 | Meyer et al. . |
| 4,883,641 | 11/1989 | Wicks et al. ............................. 422/58 |
| 4,952,373 | 8/1990 | Sugarman et al. ........................ 422/61 |
| 5,021,294 | 6/1991 | Karasawa et al. . |
| 5,219,762 | 6/1993 | Katamine et al. ........................ 422/61 |
| 5,364,766 | 11/1994 | Mach et al. ............................. 422/56 |
| 5,374,395 | 12/1994 | Robinson et al. . |

FOREIGN PATENT DOCUMENTS

| | | |
|---|---|---|
| 62-114660 | 5/1987 | Japan . |
| 6-219472 | 8/1994 | Japan . |

OTHER PUBLICATIONS

Derwent Publications Database WPI Section Ch, Week 9320 Class A92, AN93–164008 XP002013177 & JP 05 096690 A (Dainippon Printing Co. Ltd.) Apr. 20, 1993.

L. C. Lopez et al., "Synthesis, Structure, and Properties of Poly (4–Methyl–1–pentene)" J.M.S.–Rev. Macromol, Chem. Phys. C32 (3 & 4), 301–406 (1992).

European Search Report, European Patent Application No. 96303458 (Sep. 17, 1996).

*Primary Examiner*—Lyle A. Alexander
*Attorney, Agent, or Firm*—McDonnell, Boehnen Hulbert & Berghoff

[57] ABSTRACT

A test sample card has a well formed in the card body for receiving a fluid sample containing a microbiological agent or microorganism and a reagent. The test sample card has a membrane in the form of a tape covering the sample well to form a closed reaction chamber of the fluid sample and reagent and provide a barrier between the fluid sample and the atmosphere. The tape is made from polymethylpentene. The high oxygen permeable and transmissible characteristics of the tape promotes a reaction between the reagent and the microorganism. The increased growth rate exhibited by the microorganism, as compared to prior art tapes, substantially reduces the time needed to complete the test detection such as using transmittance optical analysis, for example confirm of the identity of the microbiological agent or the susceptibility of the microorganism to antibiotic agents.

8 Claims, 18 Drawing Sheets

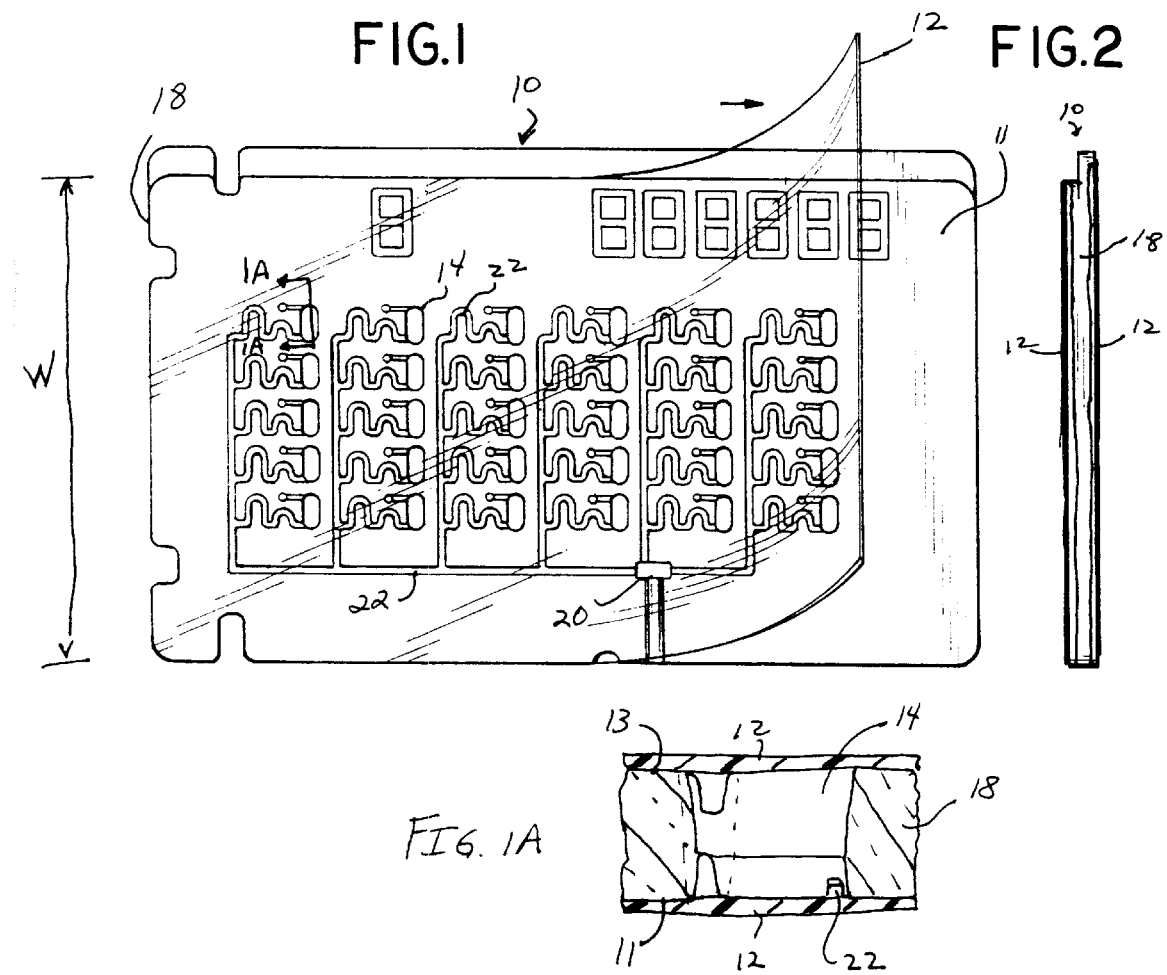

FIG. 3

UNITS OF MEASURE: SCC/100 IN²/24 HOURS / 25° C

| MATERIAL | POINT THICKNESS TESTED | O₂ TRANSMISSIBILITY (TEST VALUE) | O₂ PERMEABILITY RELATIVE VALUE (1.0 MIL) |
|---|---|---|---|
| PET (MYLAR) | 1.0 MIL | 3.9 | 3.9 |
| FEP | 1.75 MIL | 529 | 926 |
| PFA | 2.0 MIL | 710 | 1419 |
| TPX | 2.0 MIL | 2452 | 4903 |
| BOPP | 1.0 MIL | 150 | 150 |
| POLYSTYRENE | 1.0 MIL | 290 | 290 |

TEST SAMPLE CARD WITH POLYMETHYLPENTENE TAPE

RELATED APPLICATION

This is a continuation-in-part of application Ser. No. 08/455,404 filed May 31, 1995 now U.S. Pat. No. 5,800,778.

BACKGROUND OF THE INVENTION

A. Field of the Invention

This invention relates generally to the field of biological sample testing apparatus and systems, and more particularly to the subject of test sample cards which have one or more wells for containing a fluid or test sample containing a microbiological agent or organism and a reagent, and in which the well is covered and isolated from the atmosphere by a transparent membrane or tape adhered to the test sample card body to form a closed reaction chamber.

B. Description of Related Art

A variety of test sample cards are described in the patent literature which have a well or reaction site for receiving a fluid sample containing a microbiological agent, such as a microorganism, and a reagent. Several representative patents include Meyer et al., U.S. Pat. No. 4,318,994, Charles et al., U.S. Pat. No. 4,116,775; Fadler et al., U.S. Pat. No. 4,038,151 and Charles et al., U.S. Pat. No. 4,118,280, the contents of each of which are fully incorporated by reference herein. These patents describe a test sample card having a plurality of wells arranged in the test sample card body. The reagent is typically loaded in the well of the card during the completion of manufacture of the card. The reagent typically comprises a growth medium for a microbiological agent in the fluid or test sample. It is known to load a different reagent in each of the wells of the card in order to perform identification testing of a fluid sample containing an unknown microbiological agent or organism. It is also known to include in the reagent various antibiotics in order to test the microbiological agent for susceptability to the antibiotics.

In the sample testing system described in the Charles et al '280 patent, after the well of the test sample card has been loaded with the fluid sample, the card is incubated for a period of time to promote a reaction between the microorganism and the reagent, i.e., growth of the microorganism. After a period of time, the well is subject to optical analysis by a transmittance light source and a detector which are positioned on opposite sides of the well or by alternate detection methods. If the growth medium or reagent is specifically suited for or "matches up" with the particular microorganism in the fluid sample, the population of the microorganism increases substantially, or some other predetermined reaction, i.e., chemical reaction, takes place, which results in the well turning cloudy and thus having a change in light transmission characteristics. The detector determines the amount of light that is transmitted from the source through the well. By comparing the transmittance measurement over a period of time, typically several hours at least, with an initial transmittance measurement, it is possible to determine whether in fact the reagent and microbiological agent are matched by virtue of the change in transmittance measurement reaching a threshold value, such as 25 or 30 percent. The change in light transmission characteristics therefore can be used to indicate the presence of a specific microorganism in the well. Identification and susceptibility may also be detected by absorbance measurements where a fluorescent agent is provided in the growth medium.

The test sample cards descended in the above patents and used in the above process have a thin transparent membrane in the form of a tape adhered to the card body covering the wells, thereby separating the interior of the wells from the atmosphere. The tape serves to prevent the fluid sample from leaking from the wells card. The tape covers the well to prevent contaminants from entering the wells. The tape also servers as a transparent window through the well, enabling light from a light source to be transmitted through the well of the card and to impinge upon a suitable detector on the other side of the well.

Several materials have been used in the prior art for the membrane or tape used to cover the sample wells. These materials include polyfluorinated polymer films such as FEP (poly(tetrafluoroethylene-co-hexafluoropropylene)) and PFA (poly [tetrafluoroethylene-co-perfluoro(alkoxy vinyl ether)], polyethylene terepthalate or PET, commonly known as Mylar, and BOPP (biaxially oriented polypropylene). All of the above materials share a common property: they are relatively impermeable to gasses and water vapor. Such materials perform adequately in terms of their functions of sealing the well and providing a transparent barrier for the well. As a result, persons working in the art have directed their efforts at improving the sample testing process by designing improvements to the test sample cards and wells themselves, improving the quality of the reagents, and improving the design of the optical instrumentation and the illumination techniques. The design and characteristics of the specific material used to cover the wells of the test sample card has been given little attention in the prior art. Whereas the prior art failed to appreciate the role that the tape can perform in improving the test reaction process, we describe herein a test sample card construction having a polymethylpentene membrane covering the wells that can substantially reduce the time required to perform the testing of the fluid sample to identify the microorganism or to determine its susceptibility to a particular antibiotic.

SUMMARY OF THE INVENTION

The present inventors have discovered that the use of a transparent membrane made from polymethylpentene to cover the wells contributes surprisingly well to promotion of the reaction between the reagent and the microorganism, due to increased oxygen transmissibility and permeability properties of a polymethylpentene membrane, particularly when the membrane has a thickness of between 1 and about 8 mils. The promotion of the reaction between the reagent and the microorganism provided by the polymethylpentene membrane results in a substantially shortened amount of time required to incubate the test sample card and obtain the test results.

Polymethylpentene has an additional advantage over the prior art materials as a material for covering a sample well: cost. Since test sample cards are typically manufactured in very large numbers, reducing the cost of materials to manufacture a card can add up to a substantial savings.

It is accordingly an object of the invention to provide a test sample card which has a membrane covering the wells of the card to form a barrier between the fluid sample in the well and an atmosphere external of the well that promotes the reaction between a microorganism in a fluid sample introduced into the well and a reagent.

A further object of the invention is to provide a test sample card that has a membrane covering the wells of the card to form a barrier between the fluid sample in the well and an atmosphere external from the card, but which has superior oxygen permeability and transmissibility properties.

A further object of the invention is to provide a test sample card that can be manufactured at a reduced cost.

BRIEF DESCRIPTION OF THE DRAWINGS

Presently preferred embodiments will be described in detail below in conjunction with the appended drawings, in which like elements refer to like elements in the various views, and in which:

FIG. 1 is a plan view of a representative test sample card with a polymethylpentene membrane in the form of an adhesive tape being applied to the surface of the card body to cover the wells and form a closed reaction chamber;

FIG. 1A is a detailed cross-sectional view of a well of the test sample card of FIG. 1 along the lines 1A—1A of FIG. 1, showing the polymethylpentene tape defining a barrier between the fluid sample and reagent in the well and an atmosphere external of the card;

FIG. 2 is an end view of the test sample card of FIG. 1;

FIG. 3 is a table of the oxygen transmissibility and permeability properties of several membranes of a thickness between 1 and 2 mils, showing the substantially increased transmissibility and permeability of polymethylpentene (referred to by its tradename "TPX" in the table) as compared to several membranes heretofore used to cover the wells of test sample cards.

DETAILED DESCRIPTION OF THE PREFERRED EMBODIMENT

Figure 4:
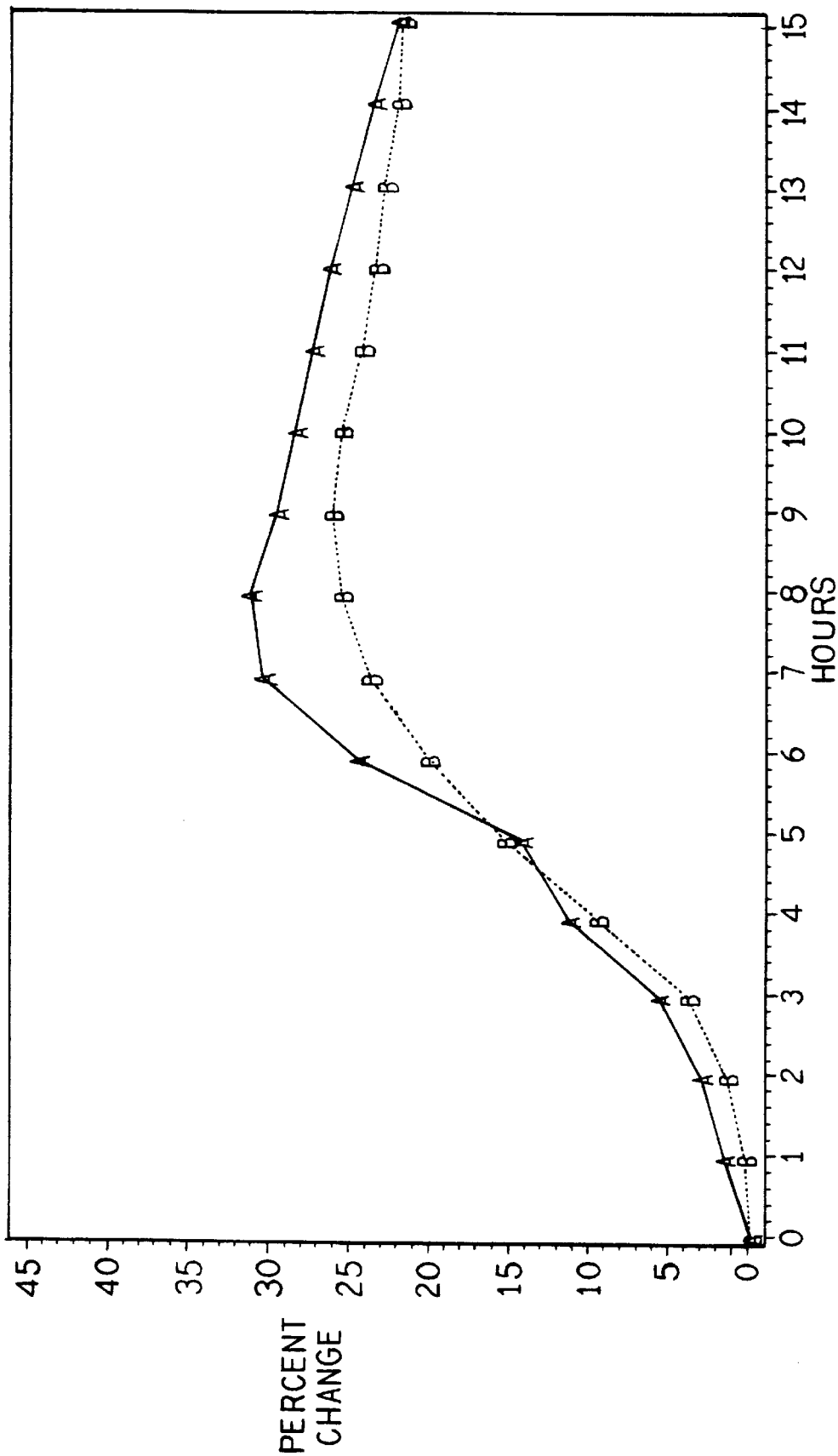
FIGS. 4–18 are graphs of the change in transmittance measurements as a function of incubation time indicating reactions between various different microorganisms and reagents or growth media for the organism in a well of the card of FIG. 1. One of the lines in the graphs represents a card with the wells covered with a polymethylpentene tape, and the other represents a card having the wells covered with a tape made from FPA. The graphs indicate that a pronounced increase in organism growth and rate of growth that occurs in the test sample card with the polymethylpentene tape, as compared to test sample cards with an FPA tape covering the wells.
Figure 5:
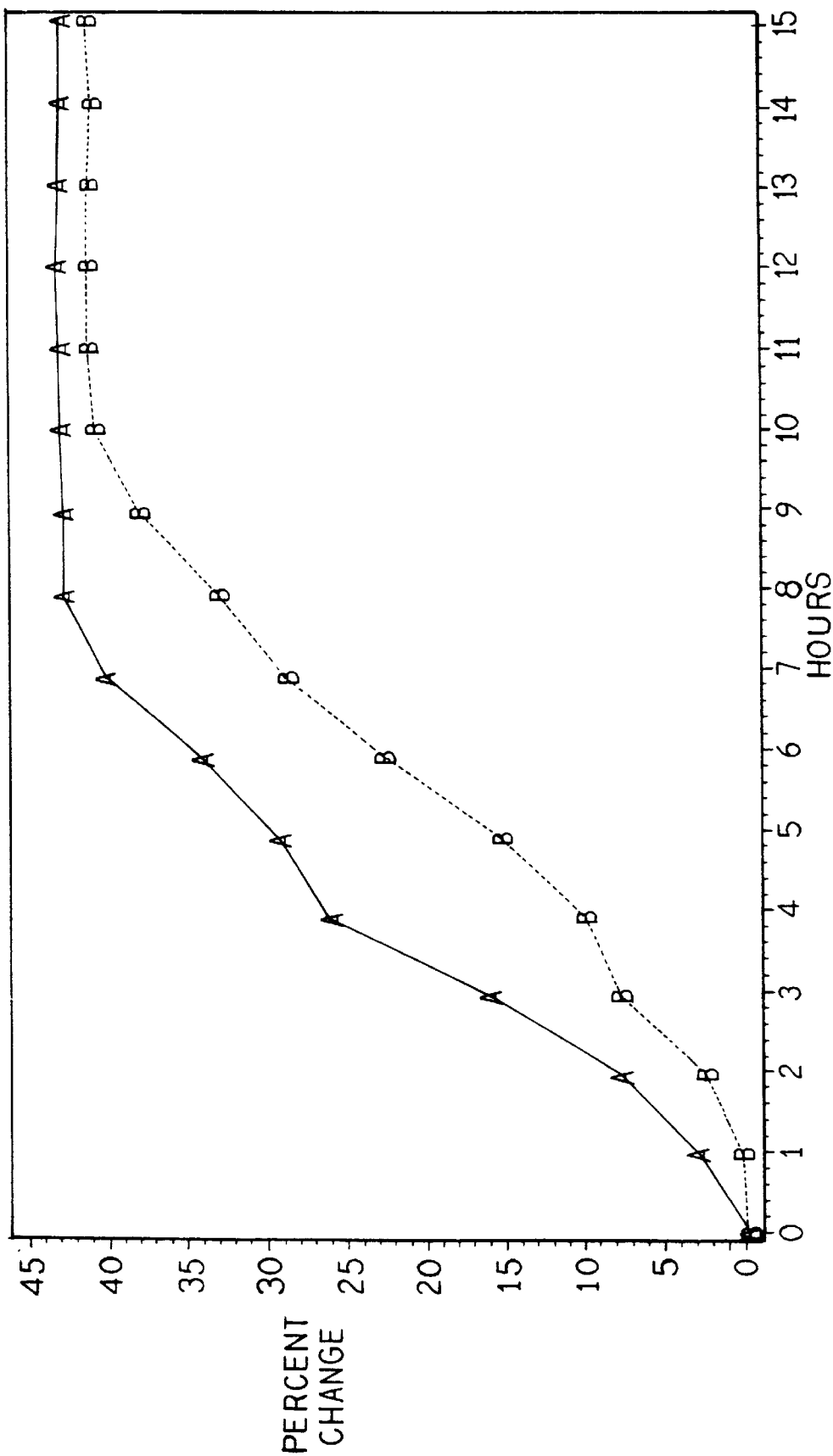
Figure 6:
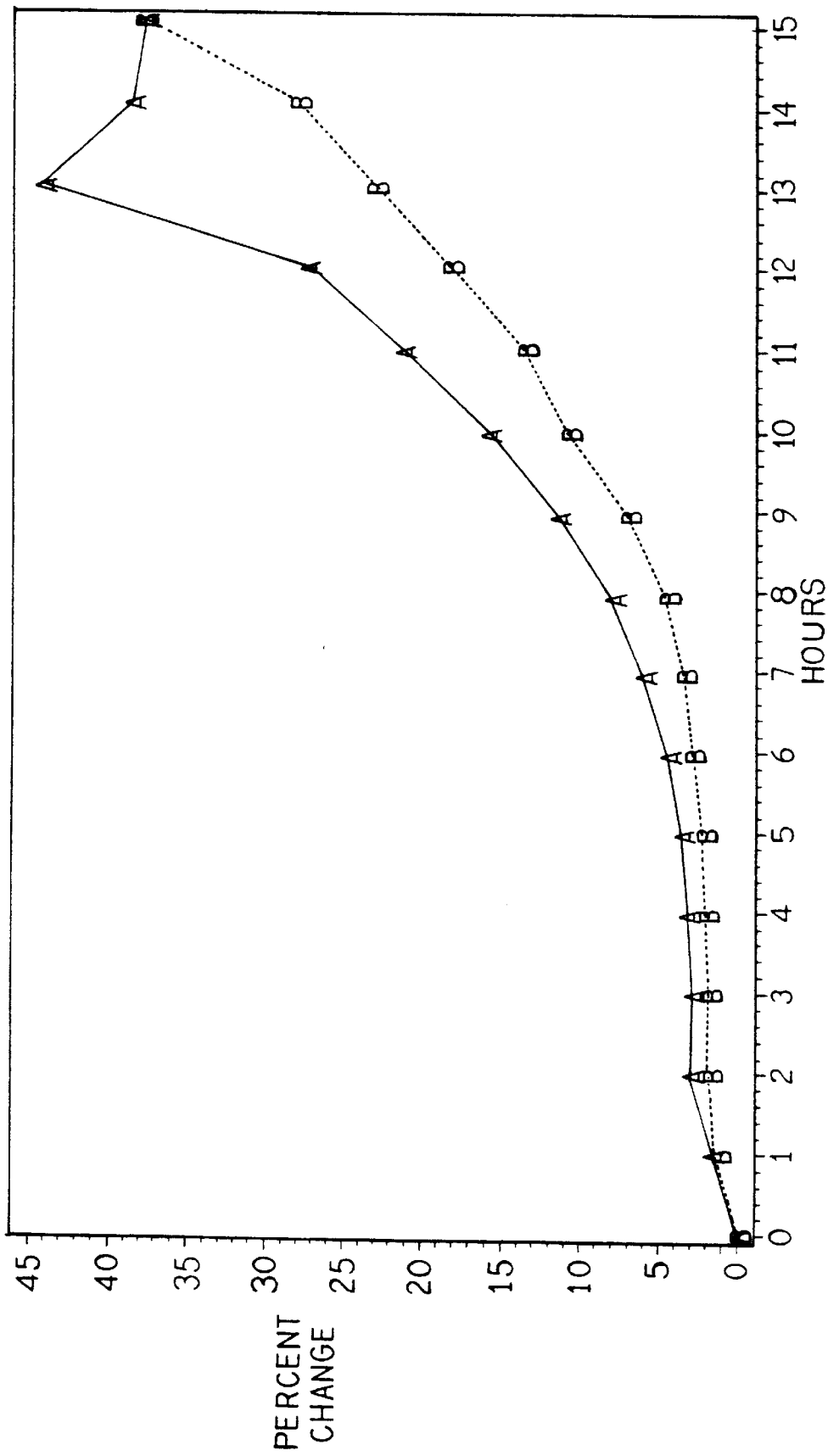
Figure 7:
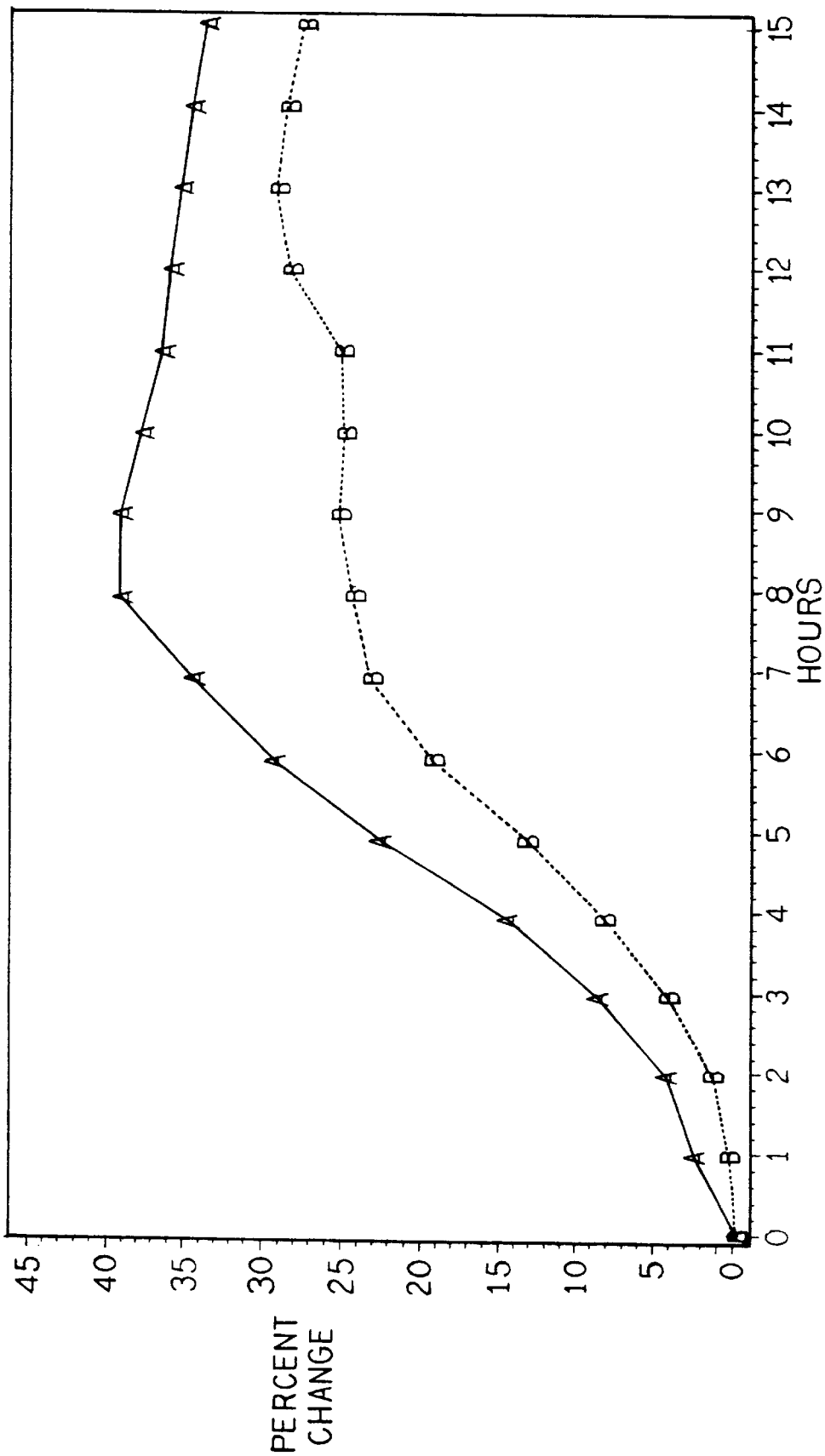
Figure 8:
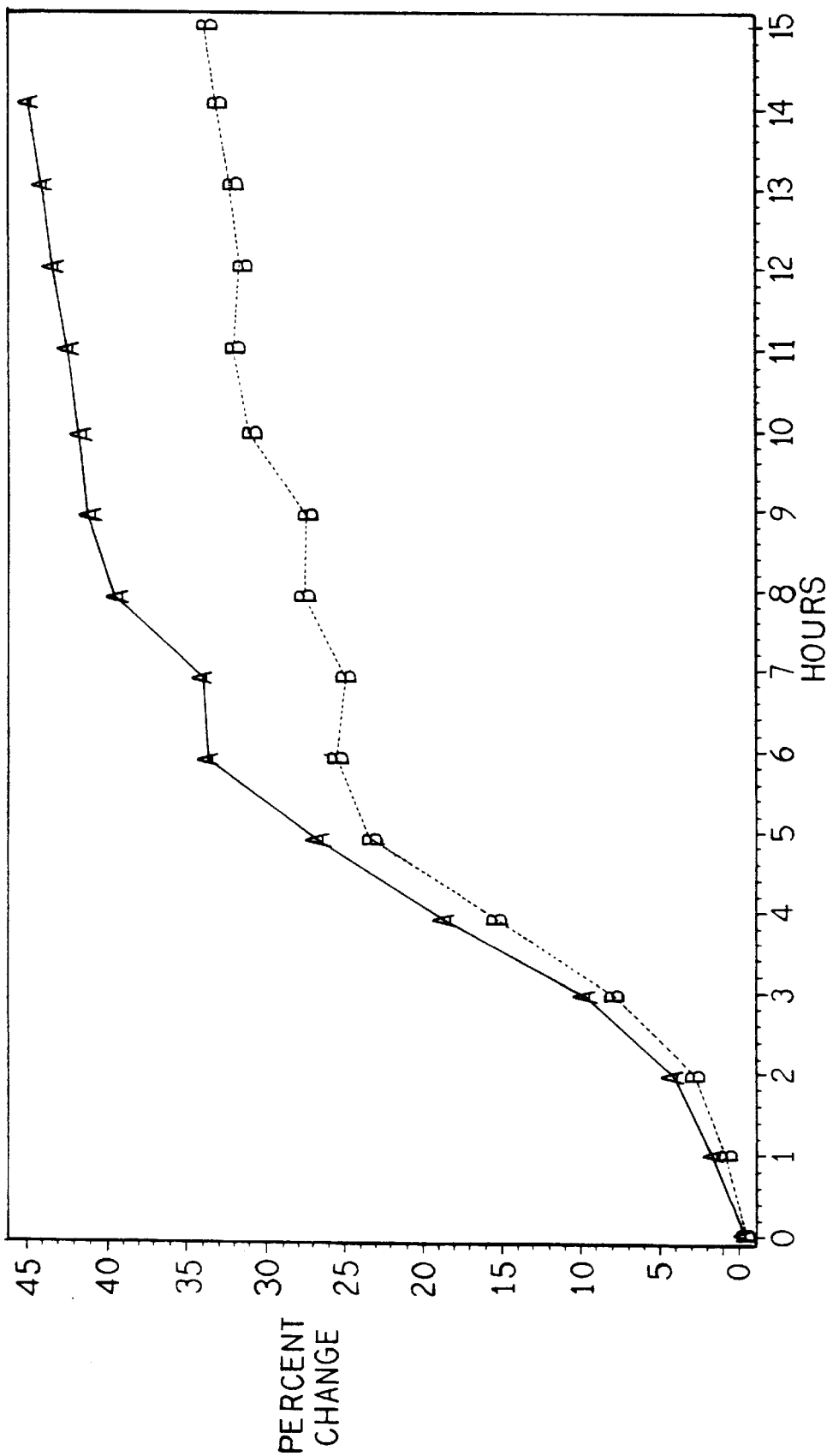

FIG. 1 is a plan view of a representative test sample card 10 with a polymethylpentene membrane 12 in the form of an adhesive tape applied to the front surface 11 of the card 10 in a manner to cover a plurality of sample wells 14 formed in the card body 16.

In the illustrated embodiment, a fluid sample is loaded into the test sample card 10 by means of a transfer tube (not shown) having one end in communication with an intake manifold 20 and the other end inserted into a receptacle such as a test tube containing the fluid or test sample. The fluid sample is conducted to each of the wells in the card 10 by means of fluid channels 22 formed in the surface 11 of the test sample card 10 and/or internal fluid channel structures. Various techniques can be used to conduct the fluid from the receptacle into the transfer tube and manifold 20 and through the fluid channels 22 to the sample wells 14, with the use of vacuum being the prevalent technique today. The fluid sample loading process, as well as the particular fluid channel structure of the test sample card allowing the fluid samples to be conducted to the wells of the card and associated structures in the surface of the illustrated embodiment, is well known in the art. The reader is directed to the above-cited patents to Meyer et al., U.S. Pat. No. 4,318,994, Charles et al., U.S. Pat. No. 4,116,775; Fadler et al., U.S. Pat. No. 4,038,151 and Charles et al., U.S. Pat. No. 4,118,280for further details. These references, particularly the Charles et al. '280 patent and the Meyer et al. '994 patent, also contain additional details, not considered important here, concerning the placement of reagents into the wells and the instrumentation for performing transmittance measurements for the card.

Presently preferred systems for preparing the samples, loading the samples in the cards, incubating the cards and reading the cards are described in U.S. patent application Ser. Nos. 08/604,461; 08/604,472; and 08/604,672, all filed Feb. 21, 1996, the contents of which are incorporated by reference herein.

The wells 14 in the preferred embodiment of the card body 18 consist of apertures extending completely through the card body 18 from one side to the other. In order to cover the wells 14 to prevent fluid leakage and prevent contaminants from entering the wells 14, it is customary and known in the art to apply the membrane or tape to both the front and rear surfaces of the card body.

FIG. 1A is a cross sectional view of one of the wells of the test sample card 10 of FIG. 1, showing an embodiment in which the polymethylpentene tape 12 is applied to both front and rear surfaces 11 and 13, respectively, of the card body 18. The polymethylpentene tape 12 is applied in a manner such that it covers all the wells of the card 10. An adhesive that is applied to the membrane adheres to the surfaces 11, 13 of the card to securely cover the wells 14. The polymethylpentene tape 12 defines a liquid barrier between the fluid sample and reagent in the well 14 (not shown) and an atmosphere external of the card, thereby providing a closed reaction chamber for the wells 14.

FIG. 2 is an end view of the test sample card 10 of FIG. 1, showing a membrane 12 applied to the front and rear surfaces of the card to thereby cover the wells and form a closed reaction chamber. While polymethylpentene can be used as the membrane or tape for both the front and rear surfaces of the card, this is not essential. Improved oxygen transmission can be achieved by applying a polymethylpentene membrane 12 to just one surface of the card body, with a conventional tape such as FPA or other material applied to the other surface to seal the well and form a closed reaction chamber. Alternatively, the card can be molded having only one surface opening for the well.

In a preferred embodiment, the invention is practiced as follows: the polymethylpentene tape is acquired from the supplier in the form of a long roll having a width essentially equal to the width of the card body. The roll of tape is installed in a card assembly and finishing station having an apparatus for injecting the wells of the card with very small quantities of reagents. The card body is molded from a suitable material and fed into the assembly station. The card passes to a first tape-applying station, where the TPX tape is applied from the roll to one surface (e.g., surface 11 in FIG. 1) of the card body 18 to cover all of the wells 14. The tape is cut and folded over the ends of the card 10. The card 10 is then turned over. The card is then fed to a reagent loading station, where a pipettor-type device is lowered into contact with the wells 14 and places a small quantity of fluid containing the reagent into the wells. The card is then fed to a second tape applying station, which applies a layer of tape to the opposite surface of the card to completely cover the wells and form the barrier between the wells and the atmosphere. The card is then sent to a drying station, where heat is applied to the card for several minutes to remove excess moisture from the wells.

Polymethylpentene is known commercially as "TPX" and is available in the form of thin film from the Mitsui Chemical Co., part no. Opulent X-22 TPX film. A background discussion of polymethylpentene as a material is found in the article of L.C. Lopez et al., "Synthesis, Structure and Properties of Poly(4-methyl-1-pentene), J. M. S.-Rev. Macromol. Chem. Phys., C32 (3&4), pp 301–406 (1992). After purchasing the film from the manufacturer, an adhesive is applied to the film in known fashion and the film is formed into a large roll of tape.

Polymethylpentene in the form of a film possesses a unique combination of properties that make it particularly effective as a membrane for covering the wells of a test sample card 10 of the general type illustrated in FIG. 1. Polymethylpentene exhibits good tensile strength, is easily handled manually or by a machine, is exceptionally clear, is light weight, and is readily manufactured in the form of thin films and in the form of a thin tape. In addition, and most significant for present purposes, polymethylpentene membranes having a thickness of between 1 and about 4 mils (thousands of an inch) possesses a relatively high oxygen permeability as compared to other known clear plastic membranes. This is significant for the present application, since the reaction of the microorganism in the well with the reagent is effectively promoted and accelerated in an environment in which an elevated concentration of oxygen is present in the well and available to the microorganism.

This point is demonstrated in FIG. 3, which is a table of the oxygen transmissibility and permeability properties of several membranes of a thickness between 1 and 2 mils, showing the substantially increased oxygen transmissibility and permeability of polymethylpentene (referred to by its tradename "TPX" in the table) as compared to several membranes heretofore used to cover the wells of test sample cards. Note that the oxygen transmissibility of polymethylpentene is markedly elevated as compared to other films, at least by a factor of three over the next alternative film, PFA. Note also that the oxygen permeability is also increased by at least a factor of three over the next alternative film.

The inventors have discovered that the increased oxygen transmissibility and permeability properties provided by a polymethylpentene membrane can be exploited in tapes of varying thicknesses, with the choice of thickness depending upon the expected incubation time and temperature and the desirability of modifying, i.e., increasing, the oxygen supply to the well 14. A thickness of 2 mils for the polymethylpentene tape 12 represents a preferred embodiment for most cards used in susceptibility and identification testing. However, the thickness of the polymethylpentene tape may be increased (such as by applying the tape in layers) to an overall thickness of, for example 4 mils, 6 mils or possibly even 8 mils and still obtain some elevated oxygen permeability and transmissibility performance as compared to alternate tapes in the prior art. As the polymethylpentene membrane is increased in thickness, the oxygen transmissibility and permeability is correspondingly reduced, however the evaporative loss of water from the well, a desirable result, is also reduced. A thickness of 1 mils provides even better oxygen transmission and permeation than 2 mils, but at a thickness of 1 mils the material presents some difficulties in application of the tape to a test sample card at high speed without formation of wrinkles in the tape. These difficulties can be overcome by using extra care in handling and applying the tape to the card, running the tape application equipment at slower speed, modifying the tape application apparatus, or by other means.

Thinner films (such as 1 and 2 mils) provide a distinct oxygen advantage in the aerobic growth of microorganisms, as compared with thicker films, such as polymethylpentene at 4 mils thickness. The magnitude of the improvement depends on the individual microorganism, as different microorganisms respond differently to the increased oxygen supply to the well. If one uses a 30% change in transmission readings from an initial reading to a second reading after incubation as a threshold indicating a positive identification, experimentation has indicated that, in some cases, the detection can be made 25% sooner by using a 2 mils polymethylpentene tape instead of a 4 mils polymethylpentene tape.

However, for prolonged incubation times (e.g., on the order of 18 hours), issues of evaporative water loss and the resultant formation of bubbles in the well must also be considered if polymethylpentene on the order of 1–2 mils are used. It has been experimentally determined that a well having a fluid volume of 30 microliters and incubated at 18 hours at roughly 35–37° C. is subject to approximately 1 microliter of water loss via evaporation from the well having a 4 mils TPX membrane (formed by adhering two 2 mil layers to each other), 2 microliters of water loss from the well having a 2 mils TPX membrane, and 3 microliters was loss from the well having a 1 mil TPX membrane. See Table 1 below.

TABLE 1

MOISTURE LOSS INCUBATING TPX TAPED 30 WELL CARDS

| Tape | Card # | Initial Weight $H_2O$ (g) | Final Weight $H_2O$ (g) | Net Loss |
|---|---|---|---|---|
| 1 mil TPX | 1 | 1.0173 | 0.9309 | 0.0864 |
| 1 mil TPX | 2 | 1.03 | 0.948 | 0.082 |
| 1 mil TPX | 3 | 1.0287 | 0.9392 | 0.0895 |
| 1 mil TPX | 4 | 0.8204 | 0.7122 | 0.1082 |
| 1 mil TPX | 5 | 1.018 | 0.9355 | 0.0825 |
| 2 mils TPX | 6 | 1.0315 | 0.9699 | 0.0616 |
| 2 mils TPX | 7 | 1.0306 | 0.9705 | 0.0601 |
| 2 mils TPX | 8 | 1.0312 | 0.9715 | 0.0597 |
| 2 mils TPX | 9 | 1.0275 | 0.9696 | 0.0579 |
| 2 mils TPX | 10 | 1.0293 | 0.989 | 0.0603 |
| 2 × 2 mil TPX | 11 | 1.0304 | 0.9958 | 0.0346 |
| 2 × 2 mil TPX | 12 | 1.0298 | 0.9977 | 0.0321 |
| 2 × 2 mil TPX | 13 | 1.0282 | 0.9944 | 0.0338 |
| 2 × 2 mil TPX | 14 | 1.0323 | 0.9993 | 0.033 |
| 2 × 2 mil TPX | 15 | 1.0262 | 0.9928 | 0.0334 |

Average Net Loss 1 mil TPX = 0.08972 g
Standard deviation = 0.010774
Average Net Loss 2 mils TPX = 0.05992 g
Standard deviation = 0.001335
Average Net Loss 4 mils TPX = 0.03338 g
Standard deviation = 0.000928

Further, a significant number of bubbles could be observed in the well covered by the 1 mil TPX membrane, whereas fewer bubbles were observed in the wells covered with TPX membrane at 2 mils and fewer still with 4 mils, although the bubbles were very small in number and size. The presence of bubbles will adversely effect detection.

Thus, very thin films on the order of 1 mils are likely to provide faster growth and markedly reduced incubation time provided they are gently handled during the process of adhering the membrane to the card body, and the incubation times are kept under 12 hours. Normal incubation times (up to 24 hours) are best accomplished with membranes in the 2–3 mils thickness. Test sample cards with membranes of this thickness of TPX will achieve substantial reduction in the overall incubation time due to the increased oxygen transmission into the well. If extended incubation is required, i.e., in excess of 24 hours and in particular in excess of 48 hours, either thicker TPX membranes (4 mils or more) or an alternative material would be preferred or even required to limit evaporative water loss. The improvement on oxygen transmissibility is less pronounced with a TPX tape of greater than 4 mils, but some reduction in incubation time is expected.

Figure 19:
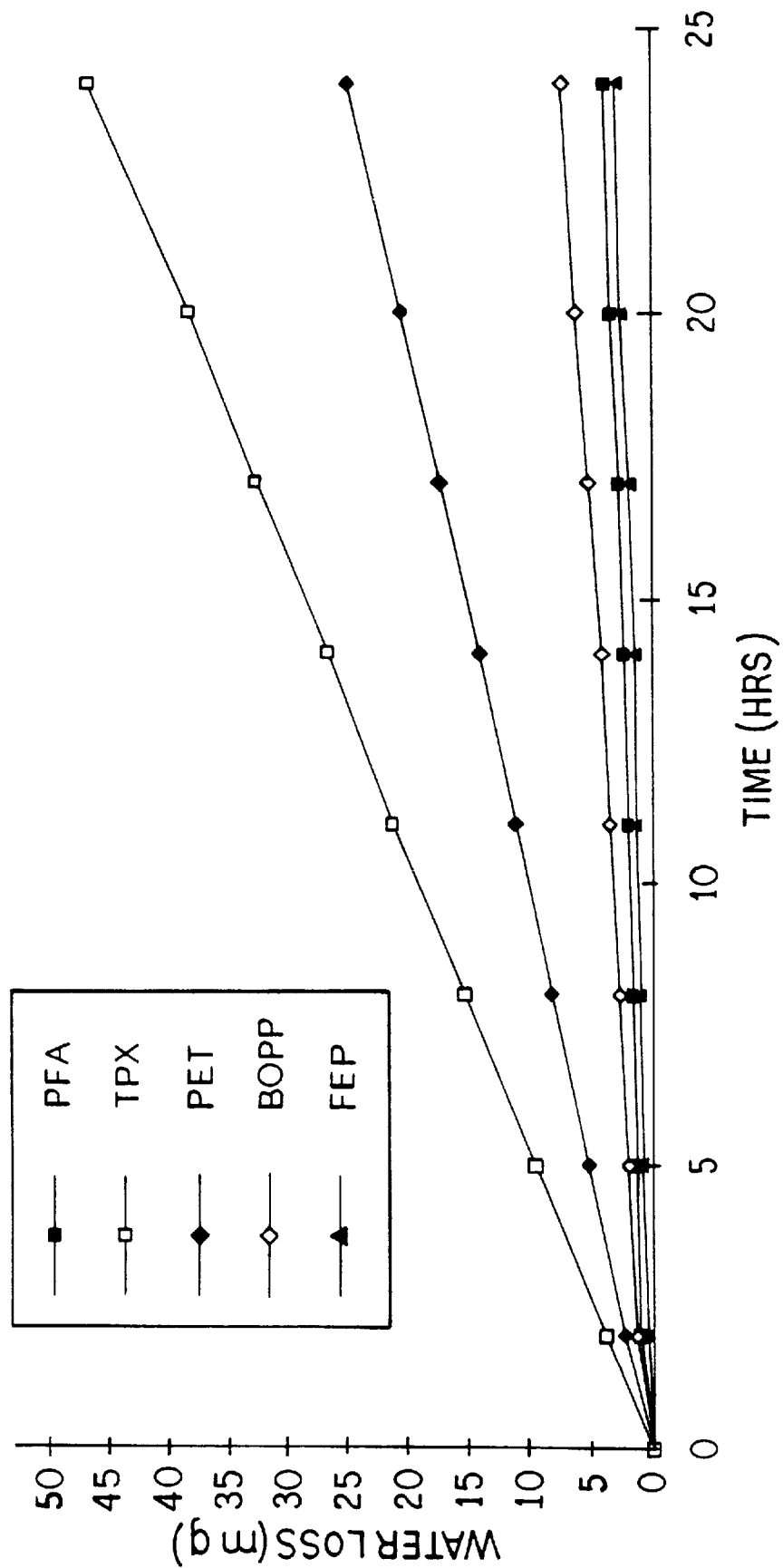
FIG. 19 is a graph illustrating that water loss through evaporation from a well as a function of time is more pronounced when is well is sealed with TPX as compared to several other types of tapes.

FIG. 19 is a graph illustrating, in general terms, the water loss from a well as a function of time that has been covered with various membrane materials. TPX exhibited substantially greater water evaporation characteristics as compared to the other membranes with longer incubation times. Thus, when selecting TPX as a membrane to cover the well, the issue of evaporative water loss from the well should be considered along with the anticipated incubation time and the thickness of the membrane selected accordingly, as explained above.

FIGS. 4–18 are graphs of the growth of various different microorganisms within a well covered by a TPX tape as a function of incubation time, as compared to a test sample card having a tape made from FPA as would be found in the prior art. The thickness of the TPX tape is 2 mils in each of the graphs. The graphs indicate that a pronounced increase in organism growth and rate of growth that occurs in the test sample card with wells covered with polymethylpentene tape, as compared to test sample cards with wells covered with an FPA tape. The growth of a microorganism in a sample well may be measured or detected by using transmittance measurements, as is well known in the art. In FIGS. 4–18, the microorganism growth (or, equivalently, reaction between the microorganism with the reagent loaded into the well) is illustrated as the mean percent change in light transmittance values through the well of a test sample card as a function of incubation time.

A principal advantage provided by the improved oxygen permeability characteristics of the polymethylpentene tape is realized by the reduction in the amount of time it takes for the detection, i.e. transmittance measurements to change by a threshold amount, such as 30%, which is a representative threshold indicating a positive test result. In FIG. 4, the TPX data (lines A—A—A) indicates that the 30% mark was obtained after an incubation time of 7 hours. In contrast, the FPA data (lines B—B—B) indicates that the 30% mark was never obtained. If the threshold for positive identification of the microorganism in FIG. 4 (*Pseudomonas aeruginosa*) is set as 25%, the level was obtained in 6 hours with the TPX card whereas it took 9 hours for the card with PFA. Thus, the test results would have been attained 3 hours earlier with the 25% threshold.

Figure 9:
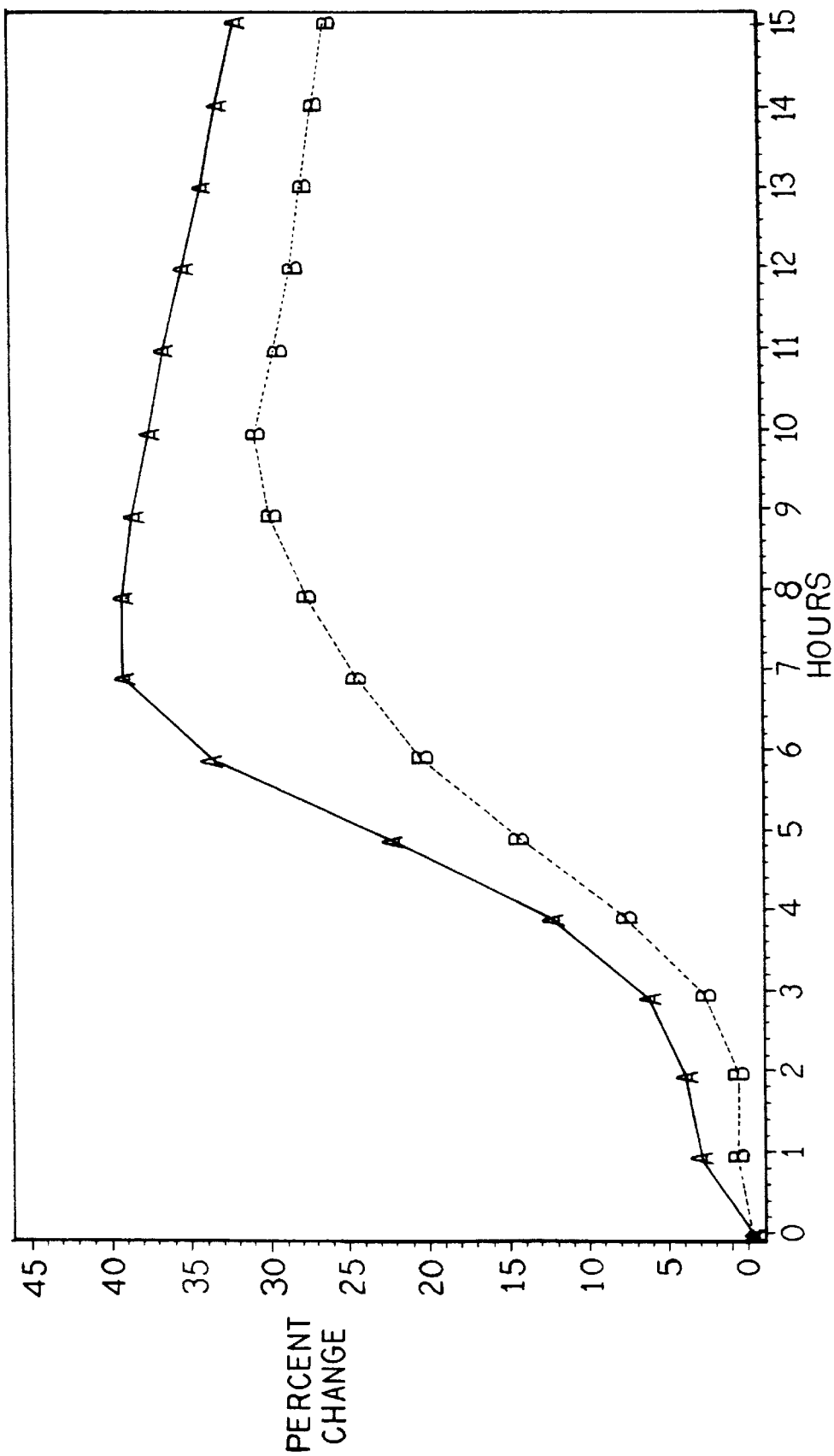

Referring to the example of FIG. 9, the 30% threshold was reached in about 6 hours for the well covered with TPX, whereas the threshold was reached in about 10 hours with a card with FPA. If a lower threshold of 25% is used, TPX outperforms FPA by several hours (from about 5 hours 15 minutes as compared to 7 hours and 45 minutes), a time savings of nearly 33%.

Figure 10:
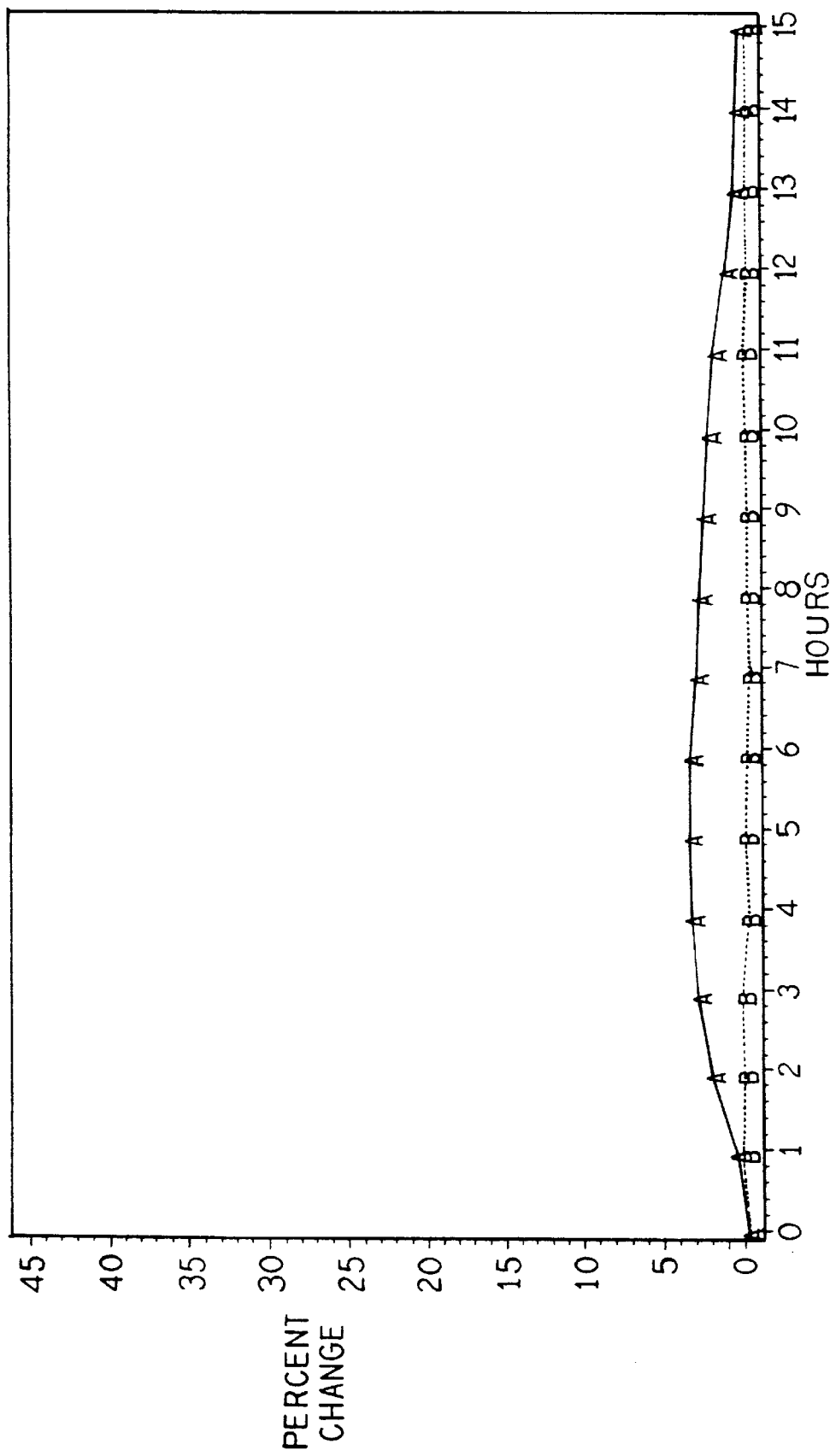
Figure 11:
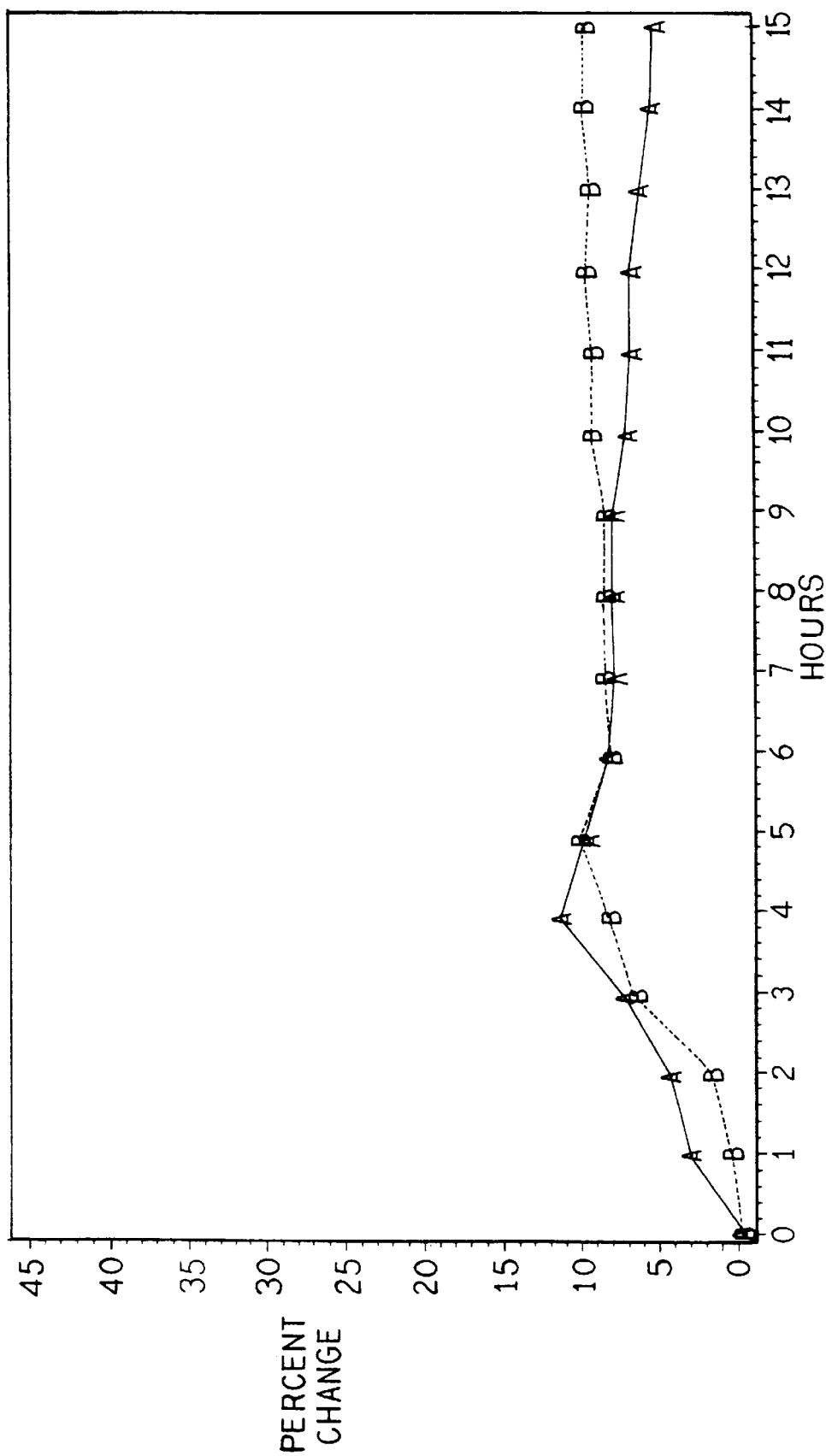
Figure 12:
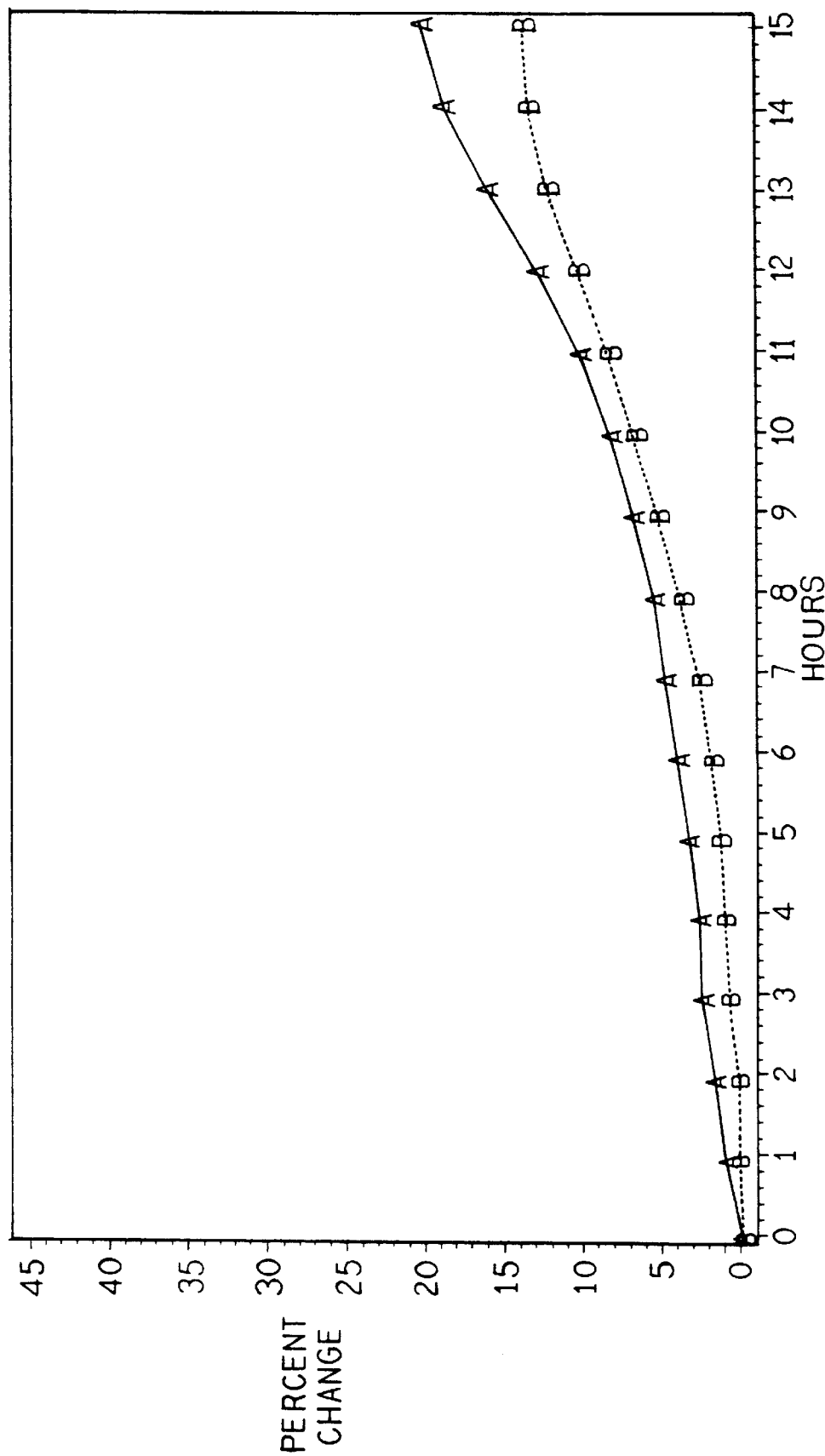
Figure 13:
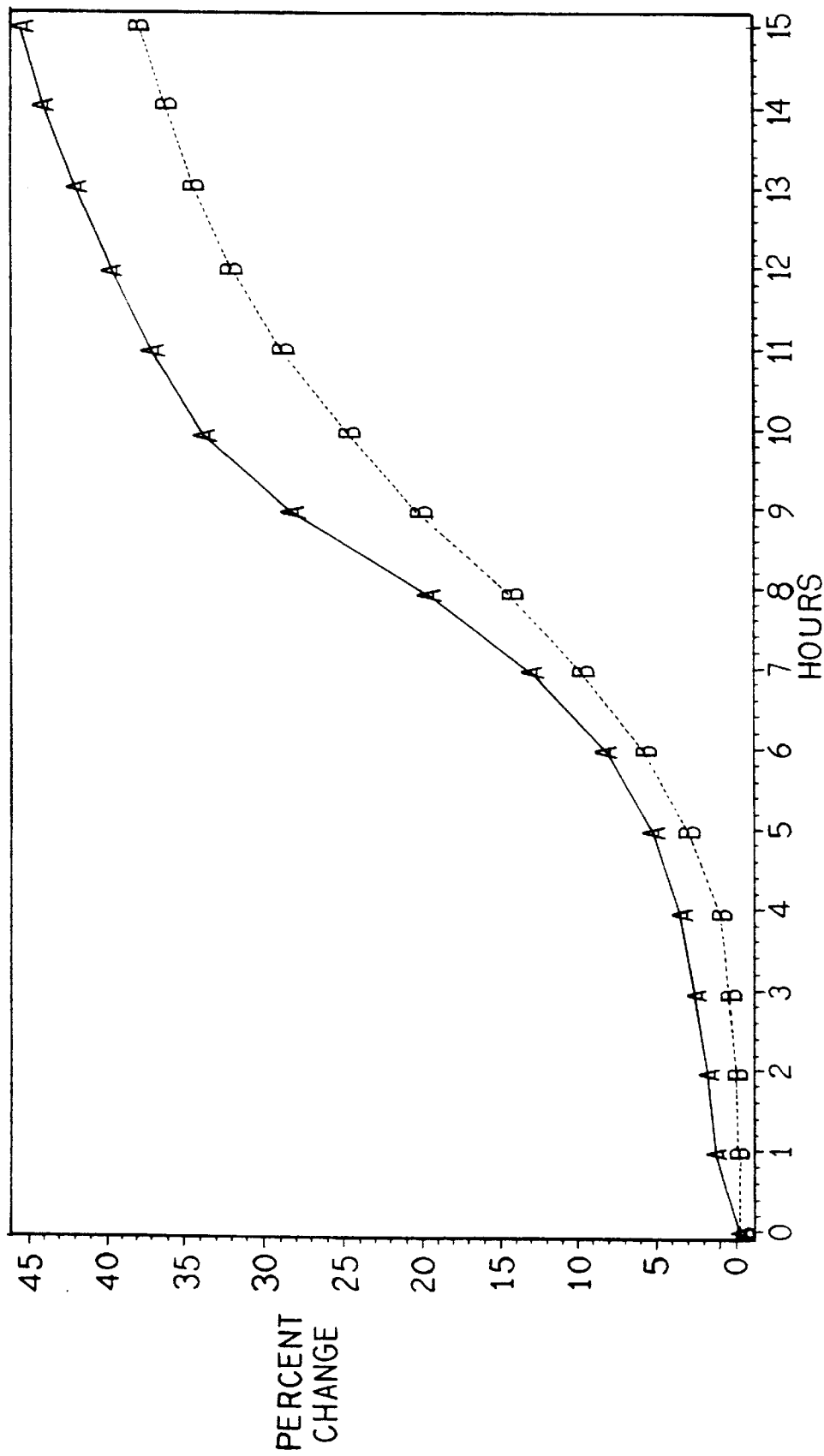
Figure 14:
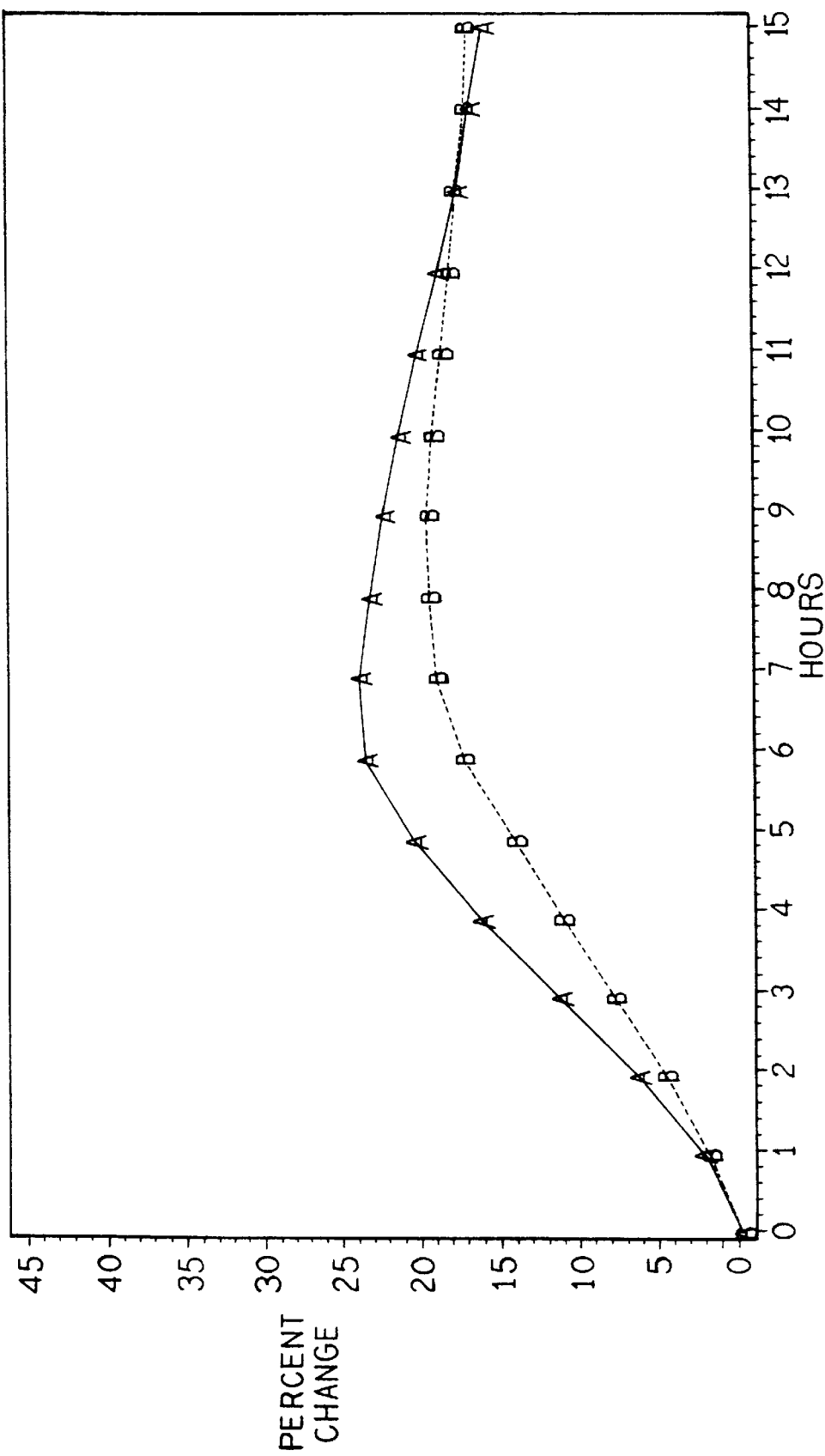
Figure 15:
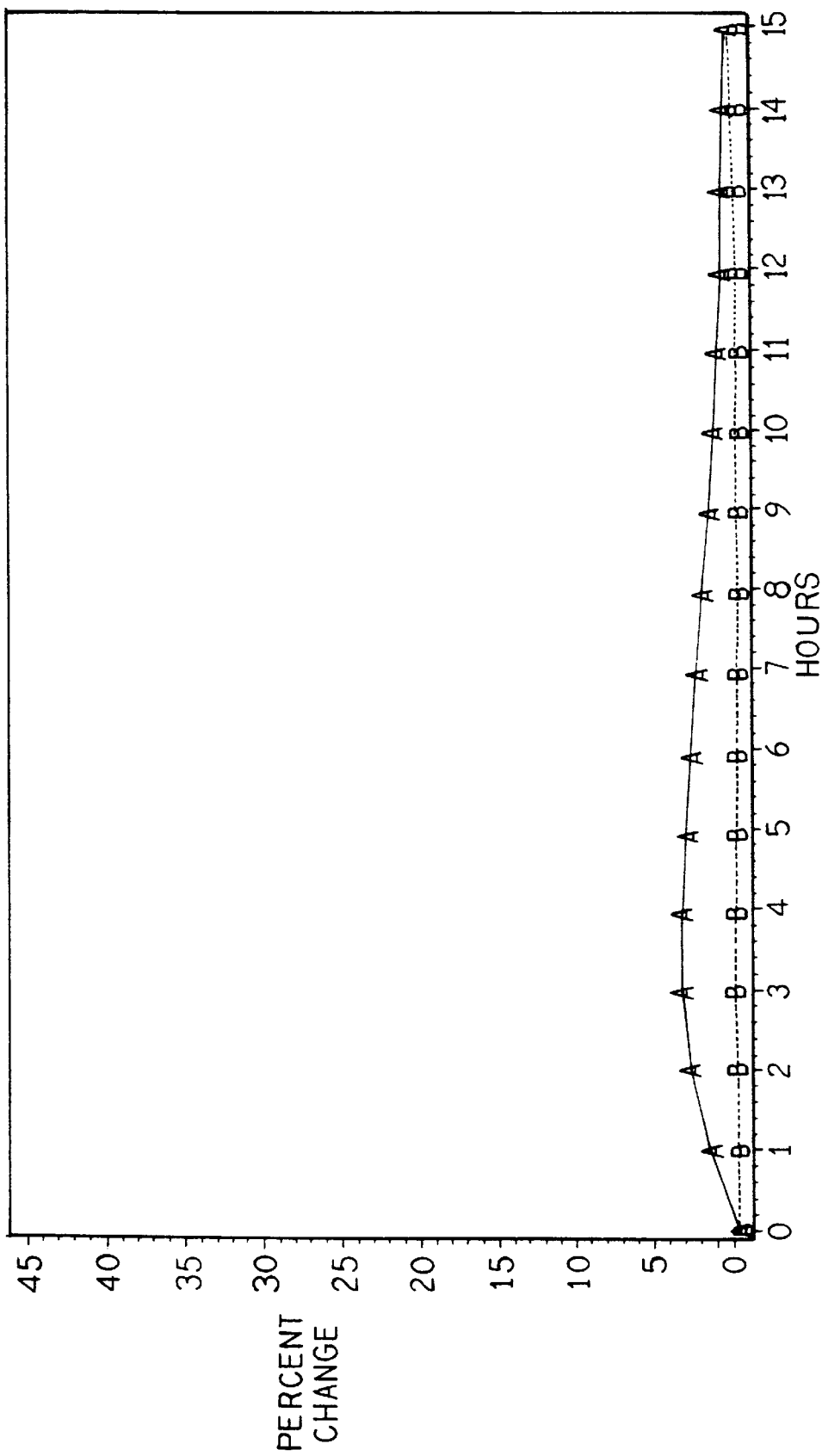
Figure 16:
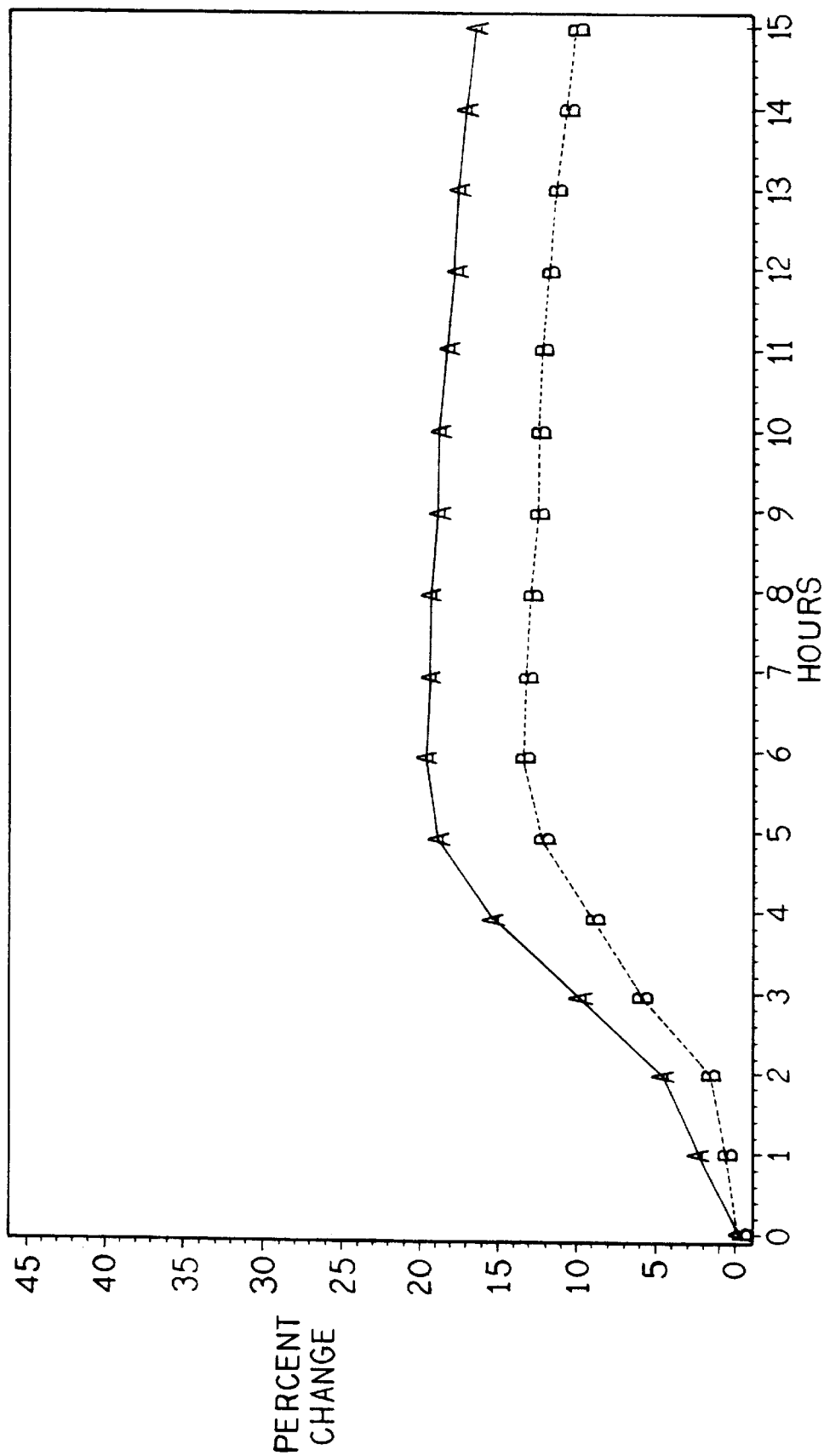
Figure 17:
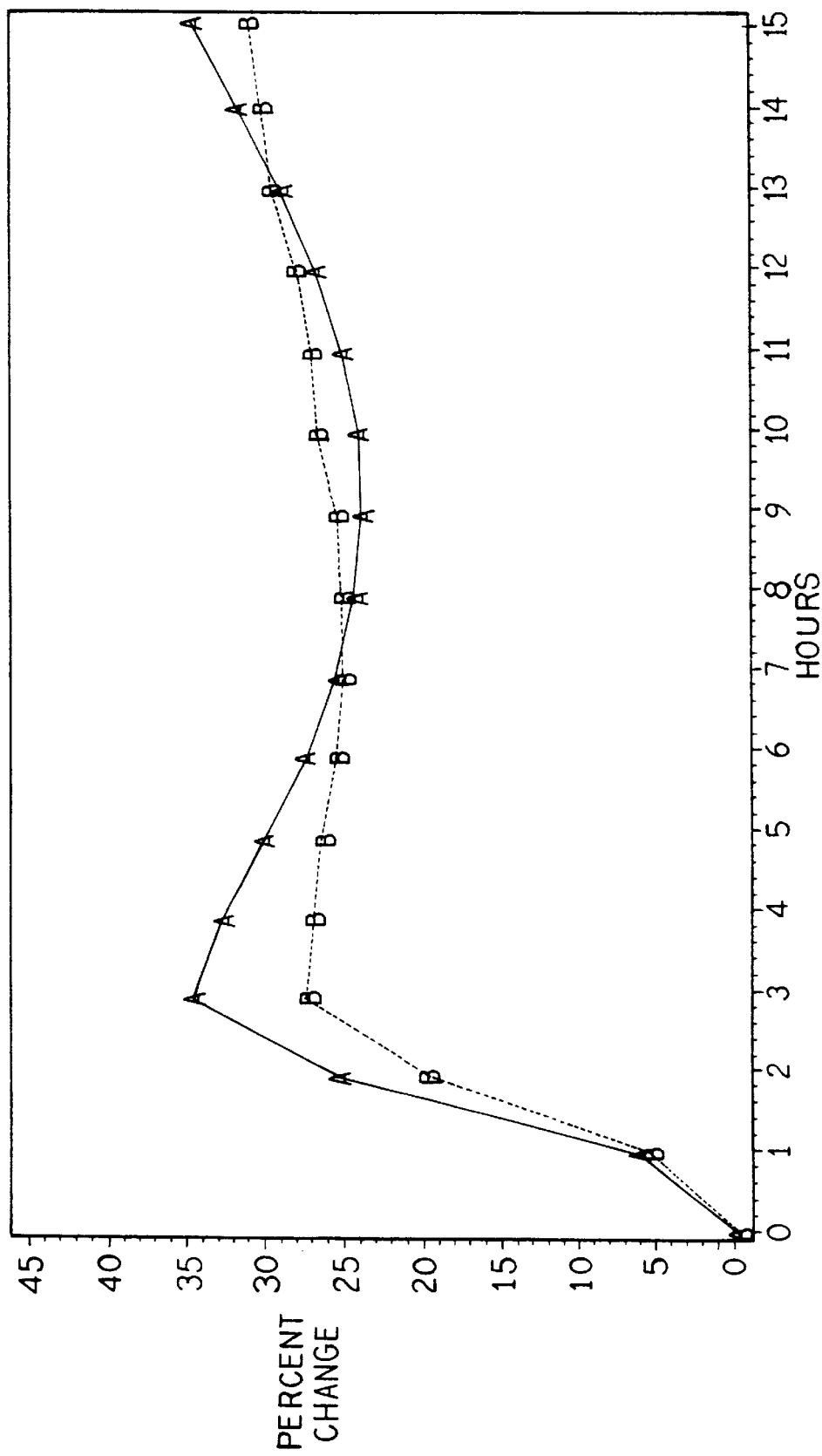
Figure 18:
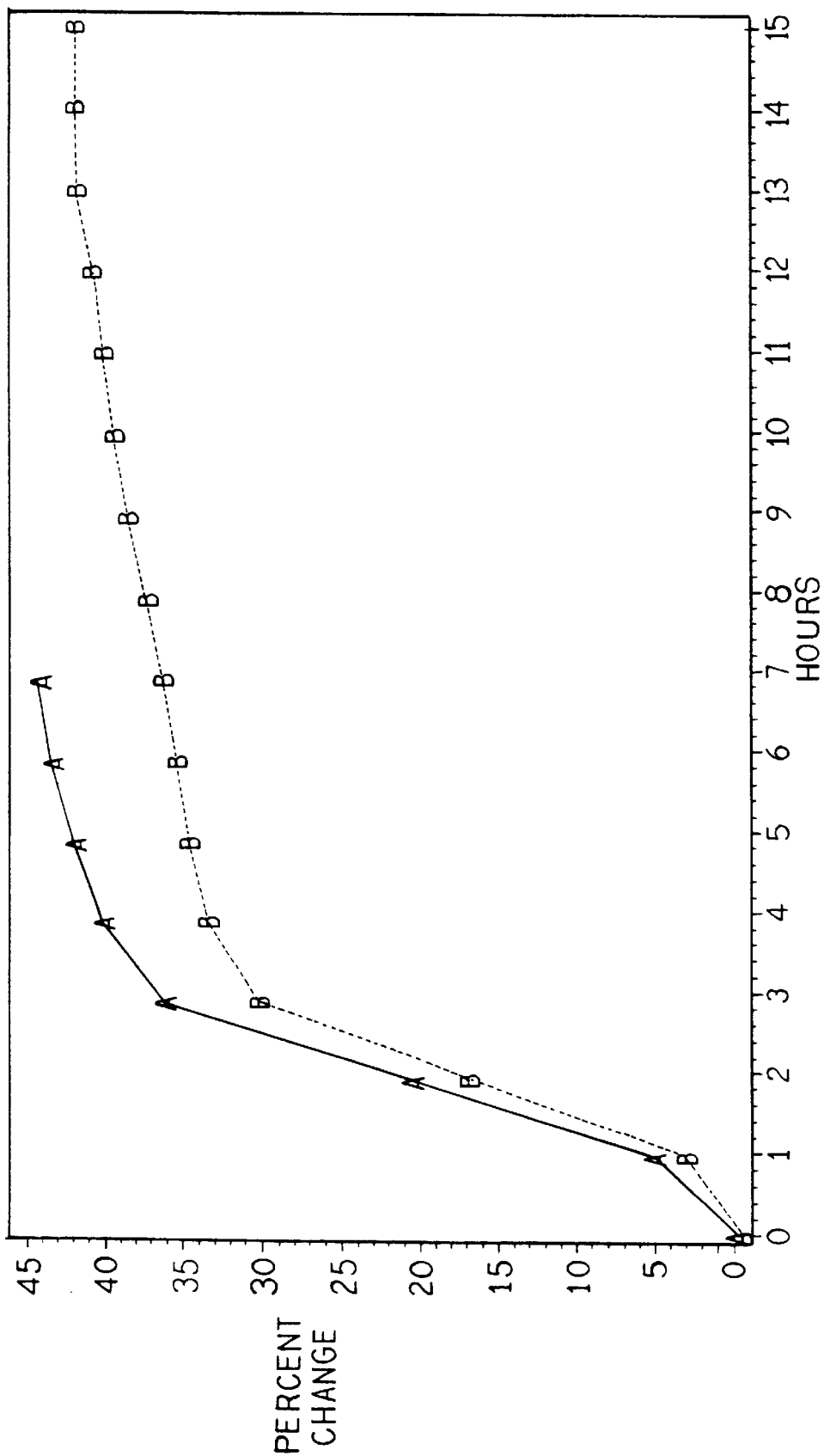

The graph of FIG. 10 is particularly significant. The organism tested, *Pseudomonas alcaligenes*, exhibited only a very slight change in transmittance measurements when PFA was used, but exhibited a substantially greater change in transmittance measurements when TPX was used. Thus, the use of TPX substantially assists in testing of microbiological agents and organisms in which rather modest transmittance changes can be expected with currently known and available reagents. New reagents do not necessarily need to be developed to improve the testing process (costing very substantial sums of money); rather, simply using TPX instead of FPA or PFT to cover the well gives the substantial improvement that one would hope for from an improved reagent. It also gives greater confidence in a positive test result for such microorganisms, since the per cent change in transmittance is significantly greater from the initial measurement and a false positive result is much less likely to be caused, for example, by environmental factors, improper preparation of the sample or reagent, drift in the optical system, cross-contamination between adjacent wells, or other types of "noise."

The preferred embodiments of the invention having been set forth, it will be appreciated that the teachings of the invention are applicable to other test sample card apparatus besides the illustrated embodiments. It is contemplated that any type of test sample card for aerobic reactions that has a closed reaction chamber and uses a tape to form a closed reaction chamber for a fluid sample and a reagent will benefit from the switch from prior art tapes to polymethylpentene. For example, the tape may be applied to the cards described in the patents cited herein, to the card described in the patent of John Staples et al., U.S. Pat. No. 5,609,828, and to other types of sample testing apparatus. Thus, various modifications may be made to the embodiments disclosed herein without departure from the spirit of the invention. This true scope and spirit is defined by the appended claims, interpreted in light of the foregoing.

We claim:

1. In a method for assembling a test sample card comprising a flat card body having front and rear surfaces and a plurality of sample wells comprising apertures formed in said card body and extending through said card body, the method comprising the steps of applying a first tape to said front surface of said card body, inserting reagents into said sample wells, and applying a second tape to said rear surface of said card body to seal said reagents in said sample wells and form a closed reaction chamber for each of said wells, the improvement comprising:

utilizing polymethylpentene as at least one of said first tape and said second tape to thereby promote a reaction between said reagent and a fluid sample introduced into said well, said polymethyl entene tape providing a high oxygen transmissible and permeable barrier between said reagent in said well and an atmosphere external of said test sample card, said polymethylpentene tape applied in a manner to be permanently secured to said card body and covering said wells in a manner so as to provide a closed reaction chamber for said reagents and a microbiological agent introduced into said wells, said polymethylpentene tape further providing a solid and liquid-phase impermeable barrier for said closed reaction chamber preventing solid or liquid-borne contaminants from entering said reaction chamber.

2. The improvement of claim 1, wherein said first tape and said second tape both comprise polymethylpentene.

3. The improvement of claim 1, wherein said polymethylpentene has a thickness of between 1 and 4 mils.

4. The improvement of claim 1, wherein said polymethylpentene has a thickness of between 2 and 4 mils.

5. The improvement of claim 2, wherein said first and second tapes each have a thickness of between 1 and 4 mils.

6. The improvement of claim 5, wherein said first and second tapes have a thickness of between 2 and 4 mils.

7. A method of assembling a test sample card having a card body defining a well, a planar surface adjacent to and surrounding said well, and a fluid passage for supplying a fluid sample to said well comprising the steps of:

adding a reagent to said well; and applying an adhesive membrane to said planar surface in a manner to securely cover said well and provide a high oxygen transmissible and permeable barrier between said well and an atmosphere external of said test sample card;

wherein said adhesive membrane comprises polymethylpentene;

said polymethylpentene adhesive membrane providing a high oxygen transmissible and permeable barrier between said reagent in said well and an atmosphere external of said test sample card said polymethylpentene membrane applied in a manner to be permanently secured to said card body and covering said well in a manner so as to provide a closed reaction chamber for said reagent and a microbiological agent introduced into said well after assembly of said test sample card said polymethylpentene tape further providing a solid and liquid-phase impermeable barrier for said closed reaction chamber preventing solid or liquid-borne contaminants from entering said reaction chamber.

8. The method of claim 7, wherein said adhesive membrane has a thickness of between 1 and 4 mils.

\* \* \* \* \*